(12) United States Patent
Schmidt et al.

(10) Patent No.: US 6,688,178 B1
(45) Date of Patent: Feb. 10, 2004

(54) ROLLER TRANSDUCER APPARATUS

(75) Inventors: Gerald E. Schmidt, Chelmsford, MA (US); John R. Hollenbeck, Fitchburg, MA (US)

(73) Assignee: Materials Systems, Inc., Littleton, MA (US)

( * ) Notice: Subject to any disclaimer, the term of this patent is extended or adjusted under 35 U.S.C. 154(b) by 42 days.

(21) Appl. No.: 10/085,276

(22) Filed: Feb. 28, 2002

Related U.S. Application Data

(60) Provisional application No. 60/273,030, filed on Mar. 2, 2001.

(51) Int. Cl.$^7$ .......................... G01N 29/24; G01N 29/26
(52) U.S. Cl. ........................................... 73/639; 73/644
(58) Field of Search ........................ 73/622, 644, 624, 73/625, 628, 635, 637, 638, 639, 597

(56) References Cited

U.S. PATENT DOCUMENTS

| | | | |
|---|---|---|---|
| 3,375,706 A | 4/1968 | Pandelis et al. | 73/612 |
| 3,384,767 A | 5/1968 | Arnold et al. | 310/366 |
| 3,780,570 A | 12/1973 | Collins | 73/600 |
| 4,122,725 A | 10/1978 | Thompson | 73/632 |
| 4,174,636 A | 11/1979 | Pagano | 73/636 |
| 4,291,577 A * | 9/1981 | Baum et al. | 73/597 |
| 4,735,087 A * | 4/1988 | Hourani et al. | 73/597 |
| 4,750,368 A | 6/1988 | Shearer et al. | 73/618 |
| 4,769,571 A * | 9/1988 | Habeger et al. | 310/334 |
| 4,858,469 A | 8/1989 | Hosgood et al. | 73/579 |
| 5,088,328 A | 2/1992 | John, Jr. et al. | 73/622 |
| 5,313,837 A | 5/1994 | Haynes | 73/622 |
| 5,437,187 A | 8/1995 | Karbach et al. | 73/635 |
| 5,493,910 A * | 2/1996 | Hall et al. | 73/597 |
| 5,760,308 A | 6/1998 | Beall et al. | 73/644 |
| 5,804,728 A | 9/1998 | Beall et al. | 73/598 |
| 6,092,418 A | 7/2000 | Schafer et al. | 73/598 |
| 6,308,570 B1 * | 10/2001 | Jackson et al. | 73/597 |

* cited by examiner

Primary Examiner—Hezron Williams
Assistant Examiner—Rose M. Miller
(74) Attorney, Agent, or Firm—Pearson & Pearson, LLP

(57) ABSTRACT

A roller transducer assembly comprises at least one core section and each core section comprises a transducer. Oil is retained within the roller transducer assembly and in particular an oil kerf isolates each core section from an outer portion of the roller transducer assembly having a nylon roller tube which is surrounded by a urethane tire outer covering. The outer portion of the roller transducer assembly rotates about each stationary core section. A pair of the ultrasonic roller transducer assemblies are arranged to provide signals for generating an ultrasonic image of an article such as a board or a log passing between the pair of ultrasonic roller transducer assemblies.

38 Claims, 9 Drawing Sheets

ROLLER TRANSDUCER APPARATUS

BACKGROUND OF THE INVENTION

This is a nonprovisional patent application claiming priority of provisional application for patent Serial No. 60/273,030, filed Mar. 2, 2001.

FIELD OF THE INVENTION

This invention relates to roller transducers and in particular to an ultrasonic roller transducer assembly which, when used in pairs, generate signals to form an ultrasonic image of an article passing between the pair of ultrasonic roller transducer assemblies.

DESCRIPTION OF RELATED ART

Wood imaging apparatus of the prior art included an air gap between the imaging apparatus and the wood, but air is a poor transmission medium for coupling acoustic energy into the wood. Because of an acoustic impedance mismatch, air is not an efficient energy transfer medium. Visual scanning with cameras had been tried to observe surface characteristics and predict the location of internal defects within the wood, but this technique was not reliable.

Prior art patents include U.S. Pat. No. 3,384,767 issued May 21, 1968 to James S. Arnold et al. and assigned to Stanford Research Institute, disclosing an ultrasonic transducer employed for evaluating a bond between materials which are fastened together and a method and means for exciting such a transducer. The transducer pairs are made of a cylinder of barium titanate having rubber around the periphery for the purpose of transmitting or receiving mechanical vibrations. The transducers are mounted to be rotatable so they can roll over a structural material such as plywood having bonds. However, it does not disclose the use of a 1–3 piezocomposite transducer disposed in interlocking core sections around which an outer tire portion rotates.

In U.S. Pat. No. 3,780,570, issued Dec. 25, 1973 to Jack T. Collins and assigned to Automation Industries, Inc., an ultrasonic inspection device is described for testing flat bonded panels such as plywood. A plurality of transmitting search units are provided on one side of the panel and a plurality of receiving search units are mounted on the opposite side of the panel. Each search unit includes a roller which is adapted to roll across the surface of the panel. An ultrasonic transducer is mounted on the drum. In order to acoustically couple the transducers to the surface of the panel, a wear receiving member such as a tire may be provided around the outer or active face of the transducer. This tire may be permanently mounted on the outside of the transducer, such as by bonding it directly thereto. The tire is preferably made from a resilient material transparent to ultrasonic energy. Also, the acoustical impedance of the tire should closely match that of the transducer. The transducer is intimately acoustically coupled to the panel. However, it does not describe a pair of ultrasonic rollers, one on each side of a panel for generating an image of the panel wherein only the outer portion of the roller rotates about a plurality of core sections each having a 1–3 piezocomposite element.

In U.S. Pat. No. 4,750,368, issued Jun. 14, 1988 to Dwayne M. Shearer et al., and assigned to Weyerhaeuser Company, a method is described for on-line nondestructive determination of the internal bond strength of composite panel products by impinging an ultrasound pulse against the panel by an upper transducer assembly and receiving a transmitted pulse at second transducer assembly. The received signal strength, temperature, and panel thickness are entered into an algorithm from which the internal bond may be calculated. Each transducer assembly comprises a piezoelectric transducer. However, it does not disclose a roller transducer comprising a plurality of adjacent interlocking core sections, each of the core sections having a 1–3 piezoelectric transducer and an outer tire portion rotating about the core section, for testing a wide surface area of a board.

In U.S. Pat. No. 5,760,308 issued Jun. 2, 1998, and U.S. Pat. No. 5,804,728 issued Sep. 8, 1998 to Frank Carroll Beall et al. and both assigned to The Regents of the University of California, an apparatus is described for detecting internal bio-deterioration in round wood materials used in various applications. The method includes the steps of securing a pulsing transducer adjacent one point on the surface of the round wood and securing a receiving transducer substantially diametrically opposite to the pulsing transducer. The ultrasonic transducer transmits ultrasonic signals through the round wood which propagate through possibly deteriorated areas throughout the wood. The receiving transducer receives the propagating ultrasonic signals, and a plurality of acousto-ultrasonic parameters contained in the received ultrasonic signals are processed and analyzed. However, they do not disclose the application of 1–3 piezocomposite transducers in a plurality of core sections with interlocking structures and having an outer portion which rotates around the core sections.

In U.S. Pat. No. 6,092,418, issued Jul. 25, 2000 to Mark E. Schafer et al. and assigned to Perceptron, Inc., a method and apparatus is described for detecting and characterizing splits in logs. A wooden log is moved in a translation direction with respect to a measurement assembly by one or more driven rollers that support the wooden members from underneath. The measurement assembly comprises a transmitting and a receiving ultrasonic transducer encased in rollers such as may roll against the surface of the wooden members. As shown in FIG. 15, the ultrasonic transducers include a transducer element held in a coupling fluid such as oil as contained by the inner surface of a rotating wheel. The outer surface of the wheel provides a series of radially extending spikes 84 to penetrate bark of the log which generally inhibits the transmission of ultrasonic energy. However, it does not describe a roller transducer having a plurality of interlocking core sections, each having a transducer and an outer tire portion which rotates about the core sections for testing a wide surface area of an object such as a board or a log.

SUMMARY OF THE INVENTION

It is therefore an object of this invention to provide an ultrasonic roller transducer assembly having an outer portion comprising a nylon roller tube surrounded by a urethane tire that rotates about an inner portion comprising a plurality of core sections having transducers.

It is another object of this invention to provide a 1–3 piezocomposite element in the transducer of each core section of the roller transducer assembly.

It is a further object of this invention to provide a fluid within the ultrasonic roller transducer assembly for providing a continuous path for the ultrasonic energy to be transmitted out of the assembly and into a scanned article.

It is still another object of this invention to provide a pair of spaced apart ultrasonic roller transducer assemblies parallel to each other for generating an ultrasonic image of an article passing between the pair of transducer assemblies.

It is an object of this invention to provide a first transducer and a second transducer adjacent to the first transducer for generating signals for transmission to a moving object such as a log and detecting reflected signals from the moving object in order to calculate the velocity of the moving object.

It is another object of this invention to provide a roller transducer having a roller tube spaced apart from a combined core/hub assembly to minimize laminar flow of the fluid in the space between the roller tube and the combined core/hub assembly thereby minimizing related electrical noise.

These and other objects are accomplished by a roller transducer assembly comprising at least one core section having at least one transducer positioned in the core section to transmit or receive signals, means for stiffening the core section and securing the core section to a hub of the assembly, a roller tube surrounding and spaced apart from the core section, the roller tube being secured to each end of the assembly, means, sealed between the roller tube and an outer portion of each core section, for providing a continuous path for energy transfer to and from the transducer, and means for constraining radial and axial movement of the roller tube at least at one end while permitting rotation of the roller tube about the hub. The core section comprises means for constraining radial movement between the core section and the hub. The roller tube comprises a material for enhancing energy transfer. The roller tube comprises an outer portion of a soft material for enhancing the continuous path for energy transfer to and from the roller transducer assembly. The energy transfer means comprises a medium for efficient signal transmission. The energy transfer means comprises a fluid. Each core section comprises a cavity for receiving the transducer or the transducer and associated electronics. Each core section comprises a hollow center portion for channeling electrical leads to a connector at an end of the assembly. Each core section comprises means for transferring impact loads from the roller tube to the stiffening and the securing means. The core section, the roller tube, and the energy transfer means comprise materials to minimize energy reflections at each interface of the materials. The assembly comprises a noncontinuous contact surface above the transducer to improve inter-element separation. The roller transducer assembly further comprises means for generating and processing signals to and from the transducer. The roller transducer assembly further comprises a second transducer positioned adjacent to the first transducer in each core section, means for generating a first signal coupled to the first transducer for transmission to the object moving in a predetermined direction adjacent to the transducer assembly, means for detecting the first signal reflected from the moving object, means for generating a second signal coupled to the second transducer for transmission to the object, means for detecting the second signal reflected from the moving object, and means for calculating the velocity of the moving object from the propagation time of the detected first signal and the detected second signal sent to and reflected from the moving object.

The objects are further accomplished by an apparatus for producing an image of an object comprising a first roller transducer assembly having at least one core section, each core section comprises a transducer for transmitting signals toward the object, a second roller transducer assembly, positioned a predetermined distance from the first roller transducer assembly, comprises at least one core section and each core section comprises a transducer for receiving signals transmitted by the first roller transducer through the object moving between the first roller transducer assembly and the second roller assembly, means for processing the signals received by the second roller assembly, and means connected to the processing means for displaying an image of the object.

The objects are further accomplished by an ultrasonic roller transducer assembly comprising a plurality of core sections, each of the core sections comprises a transducer positioned in each of the core sections to transmit or receive signals, a plurality of rods, each of the rods passes through one of a plurality of rod holes on the core sections, each of the plurality of rods being secured to the assembly at each end of the rods, a roller tube surrounding and spaced apart from the plurality of core sections, the roller tube being secured to an end cap of the assembly, a tire encircling the roller tube for contacting an object, a fluid, sealed between the roller tube and the outer portions of the plurality of core sections, for providing a continuous path for energy transfer to and from the transducer of the core sections, and a bearing positioned around a neck of a hub attached to each end of the assembly enabling the tire and the roller tube to rotate about the plurality of core sections. The core sections comprise a stiff, engineering polymer, such as Delrin (Registered Trademark of E. I. DuPont de Nemours and Company of Wilmington, Delaware). Each of the plurality of core sections comprises means for interlocking adjacent core sections. The transducer comprises an acoustic transducer made from piezoelectric material or electrostrictive material. The roller tube comprises a stiff, acoustically-transmitting polymer material, such as nylon. The tire comprises a compliant acoustically-transmitting polymer, such as soft polyurethane. The fluid comprises an inert, insulating liquid, such as silicone oil. Each of the plurality of core sections comprises a cavity for receiving the transducer and a foam section disposed adjacent to the transducer for providing a low impedance backing to reflect energy out of the core sections. Each of the plurality of core sections comprises a hollow center portion for channeling electrical leads to a connector at an end of the assembly. Each of the plurality of core sections comprises a roller bearing positioned around each of the rods passing through the core sections for absorbing impact loads from the object. The plurality of core sections, the roller tube, the tire, and the fluid comprises approximately the same acoustic impedance for minimal reflections at each material interface. The tire comprises a plurality of notches above the transducers to improve inter-element separation. The ultrasonic roller transducer assembly further comprises means for generating and processing signals to and from the transducer.

A roller transducer comprising a combined core/hub assembly having a flat surface on a portion of the circumference of the roller transducer, a hollow cylindrical center portion, and an insert secured to the flat surface, a cavity disposed in the roller transducer under the inset, a transducer assembly positioned in the cavity under the insert having electrical leads which are fed to the hollow cylindrical center portion of the roller, a roller tube surrounding and spaced apart from the combined core/hub assembly, the roller tube being secured at each end of the roller transducer, and a fluid, sealed between such combined core/hub assembly and the roller tube, for providing a continuous path for energy transfer to and from the transducer assembly. The insert comprises a flat inner surface and a flat outer surface. Also, the insert comprises an outer spherical surface and an inner flat surface or an outer trapezoidal surface and an inner surface having a cavity for receiving a portion of the transducer assembly. The transducer assembly comprises a piezoelectric or an electrostrictive transducer, preferably a 1–3 piezocomposite transducer.

The objects are further accomplished by an acoustic velocity sensor positioned in a cavity of an ultrasonic roller transducer assembly comprising a first transducer, a second transducer positioned adjacent to the first transducer, means for generating a first signal coupled to the transducer for transmission to an object moving in a predetermined direction adjacent to the ultrasonic roller transducer, means for detecting the first signal reflected from the moving object, means for generating a second signal coupled to the second transducer for transmission to the moving object, means for detecting the second signal reflected from the moving object, and means for calculating the velocity of the moving object from the propagation time of the detected first signal and the propagation time of the detected second signal sent to and from the moving object.

The objects are further accomplished by the method of providing a roller transducer assembly comprising the steps of providing at least one core section having at least one transducer positioned in each core section to transmit and to receive signals, stiffening the core section with means extending through each core section and securing the extending means and the core section to a hub of the assembly, positioning a roller tube around and spaced apart from each core section, the roller tube being secured to each end of the assembly, providing a fluid between the roller tube and an outer portion of each core section to have a continuous path for energy transfer to and from the transducer, and constraining radial and axial movement of the roller tube at least at one end which permits rotation of the roller tube about the hub.

BRIEF DESCRIPTION OF THE DRAWINGS

The various objects, advantages and novel features of this invention will be more fully apparent from a reading of the following detailed description in conjunction with the accompanying drawings in which like reference numerals refer to like parts, and in which.

DESCRIPTION OF ILLUSTRATIVE EMBODIMENTS

Figure 1:
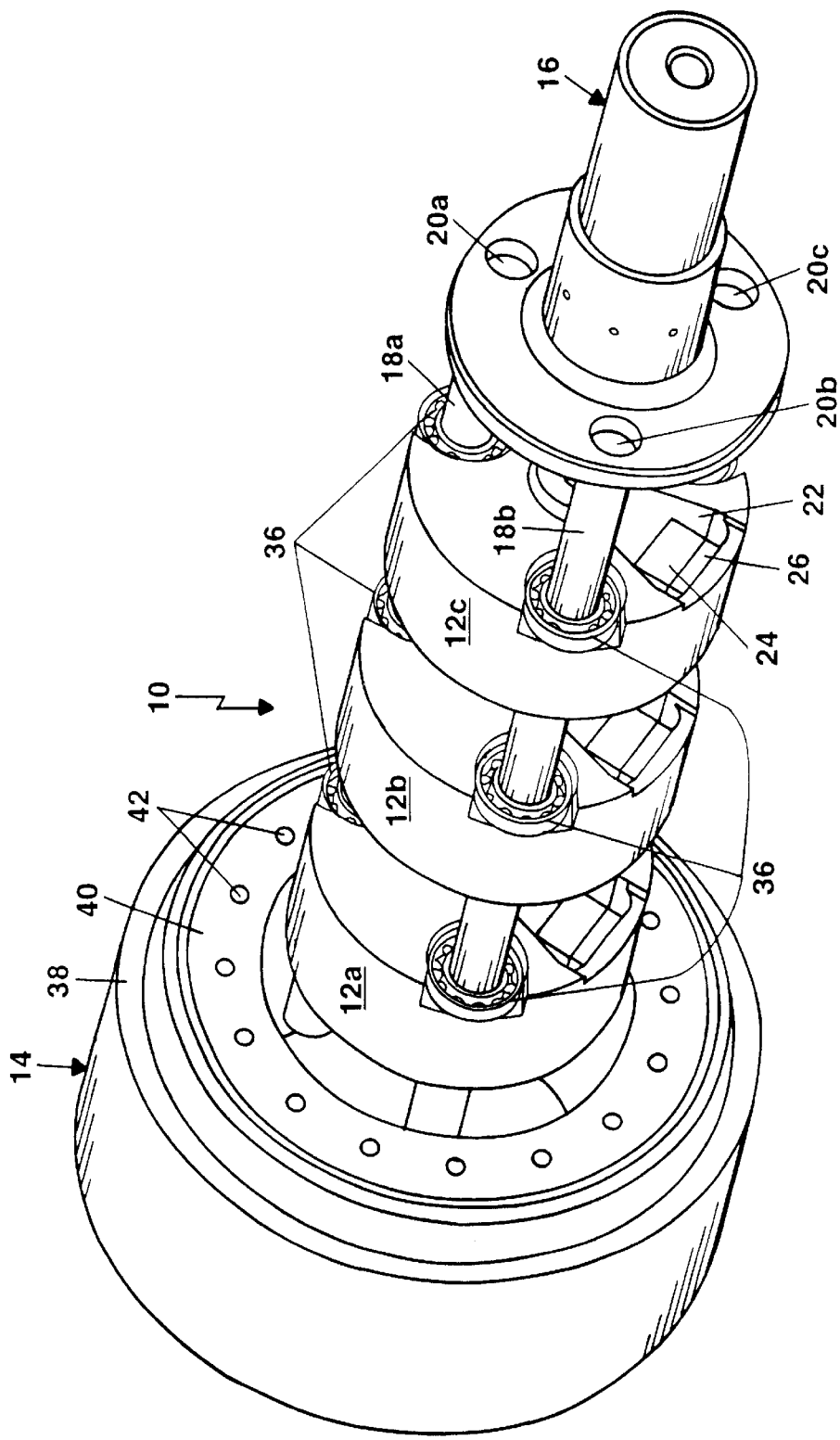
FIG. 1 is an exploded perspective view of the invention of an ultrasonic roller transducer assembly having a plurality of core sections.

Referring to FIG. 1, an exploded perspective view is shown of an ultrasonic roller transducer assembly 10 comprising a plurality of modular core sections 12a, 12b and 12c, although only three core sections are shown in FIG. 1. The preferred embodiment herein comprises fourteen core sections 12a–12n; however, the number of core sections may vary depending on a particular application.

The ultrasonic roller transducer assembly 10 is used to scan wood or other low acoustic impedance media for voids, knots or other defects. By using multiple transducer assemblies 10 an image can be formed of the interior of an object from the electrical signals received from the assemblies 10.

Figure 6:
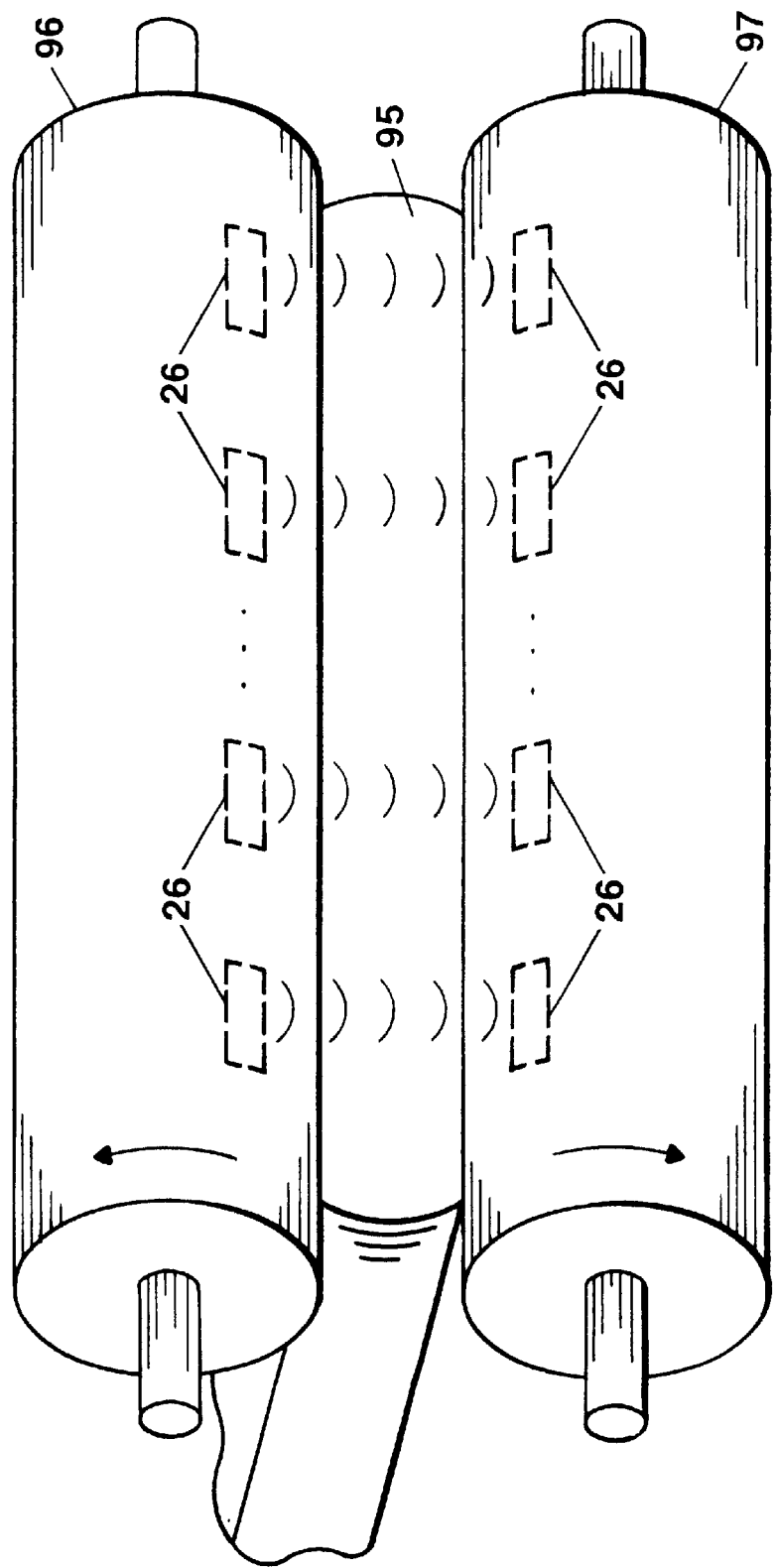
FIG. 6 is a perspective view of a pair of the ultrasonic roller transducer assemblies positioned parallel to each other having a board passing between the transducer assemblies.

Referring to FIG. 6, a pair of roller transducers 96, 97 are used to produce ultrasonic images of a board 95 to avoid cutting through defects such as knots, etc. One ultrasonic roller transducer assembly 96 is a transmitter and the other ultrasonic roller transducer assembly 97 is a receiver, and the data from the assemblies 96, 97 is processed to obtain the image which is then analyzed for detection of defect locations. Such an image can be used to optimize how raw materials are cut-up into final products.

Referring again to FIG. 1, a first end of the ultrasonic roller transducer 10 is referred to as a fill end 14 because this is the end where oil such as silicone oil is poured into the ultrasonic roller transducer assembly 10. The opposite end 16 is referred to as a connector end 16 wherein an external electrical connector attaches thereto. Three steel tension rods 18a, 18b and 18c (18c is not shown) are inserted into rod holes 20a, 20b, 20c, respectively, and positioned around each core section. Bolts are inserted into each end of the three rods 18a, 18b and 18c (18c is not shown) to secure the core sections 12a, 12b, 12c within the assembly 10. The tension rods 18a, 18b and 18c are positioned toward the outer regions of the core sections 12a, 12b, 12c to provide space for housing electronics.

Figure 2:
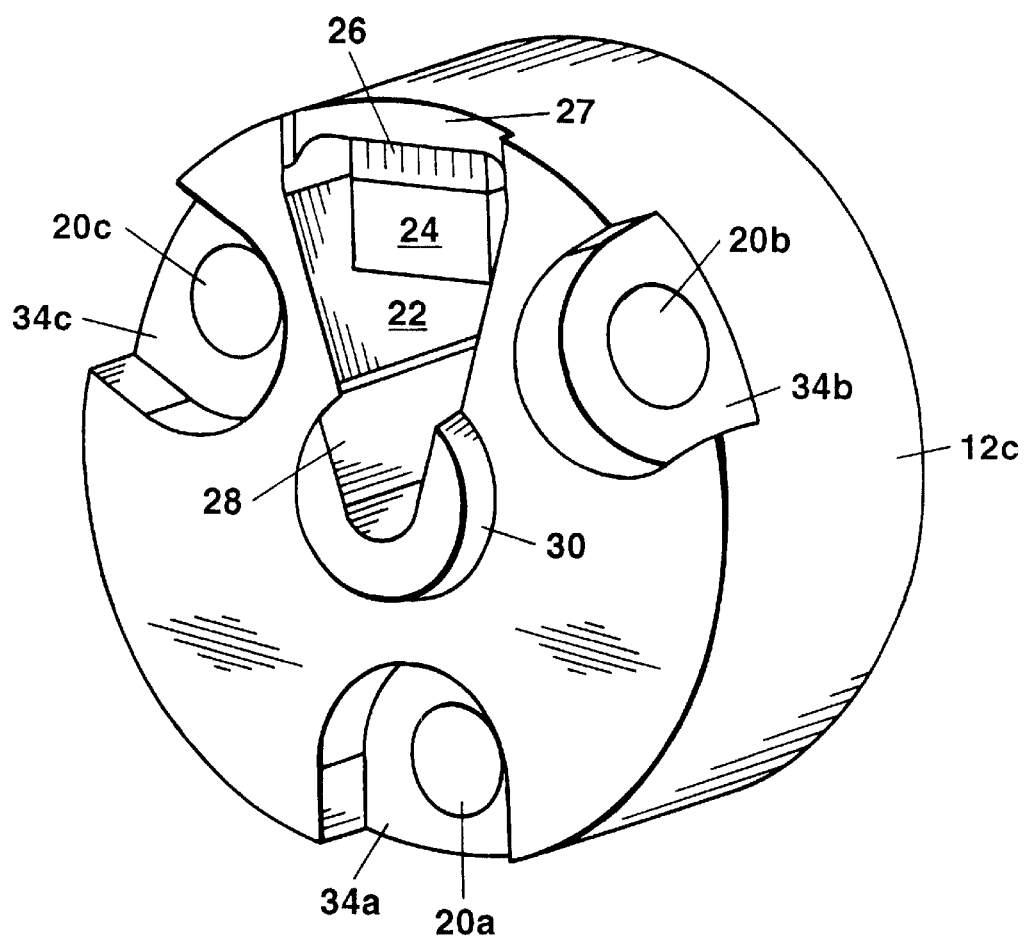
FIG. 2 is a perspective view of a core section of the ultrasonic roller transducer assembly of FIG. 1.

Referring to FIG. 1 and FIG. 2, FIG. 2 is a perspective view of one of the core sections 12a, 12b and 12c. A cavity 22 is provided within each of the core sections 12a, 12b, 12c and each cavity 22 comprises a foam section 24 disposed adjacent to a transducer 26. The foam section 24 provides a low impedance backing that reflects energy off of the interface. This ensures that the energy is directed out into the article being scanned, and not back into the roller transducer assembly 10. The transducer 26 is positioned facing the stiff polymer material of the outer portion of the core section 12c. Electrical leads (not shown) from the transducer 26 are channeled into the center hollow portion 28 of the core section 12c and such leads are fed through each core section 12a, 12b, 12c to the connector end 16 of the ultrasonic roller transducer 10. Preamplifiers and multiplexing electronics may be included in the cavity 22 area or within the center hollow portion 28.

Each core section 12a, 12b and 12c comprises an interlocking structure 30 protruding around the center hollow portion 28 of the core section 12c. The opposite side of the core section 12c comprises a receiving cavity 32 for receiving the protruding interlocking structure 30 of an adjacent core section, for example, core section 12b. The interlocking surfaces are conically tapered to provide a press-fit between adjacent core sections 12a, 12b and 12c. The interlocking structure 30 prevents tolerance stack-up or radial misalignment based on the plurality of the core sections 12a, 12b, 12c positioned tightly adjacent to each other. This is important for minimizing the total "runout" (eccentricity) of the ends of hubs 64, 84 (FIG. 4) which leads to higher bearing stress thereby reducing the life of the larger primary bearings.

Figure 7:
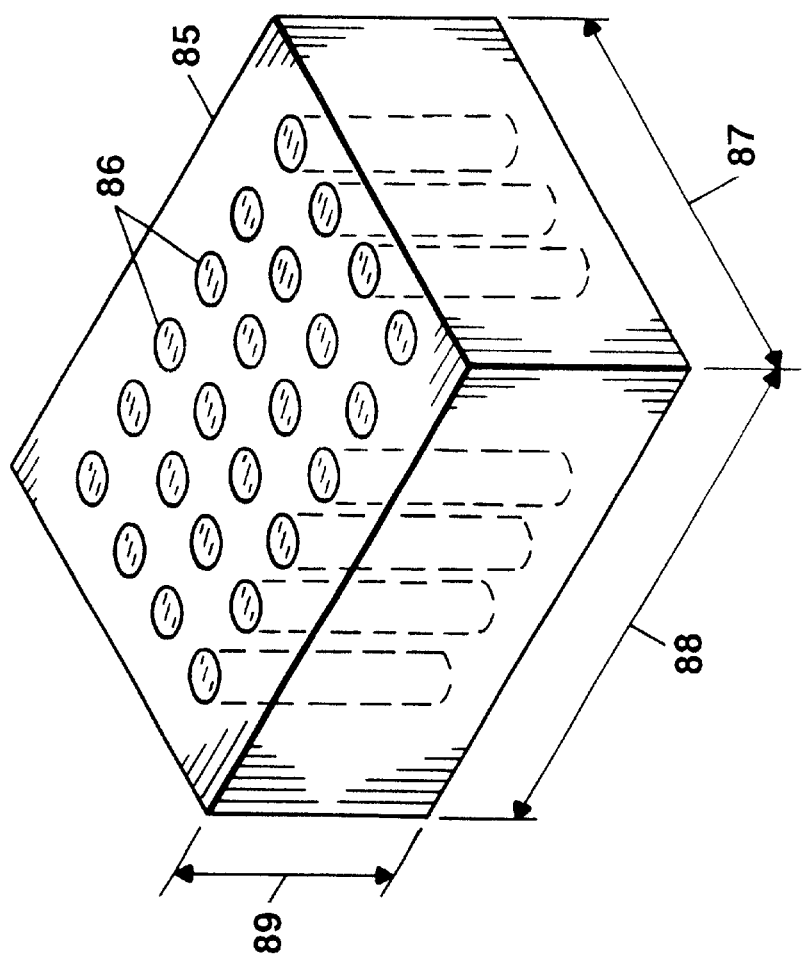
FIG. 7 is a perspective view of a 1–3 piezocomposite element of the transducer enclosed within each core section of the ultrasonic roller transducer assembly.

Referring to FIGS. 2, 6 and 7, the transducer 26 comprises a 1–3 piezocomposite element 85 as shown in FIG. 7. This element 85 is a group of piezoelectric ceramic rods 86 embedded in a polymer matrix. The piezoelectric ceramic rods 86 extend through the thickness 89 of the element 85 and are poled in this direction. The thickness 89 of the element 85 is selected to provide a 200 Khz resonance frequency (within an operating range of 10 Khz–10 Mhz). The length 88 and width 87 of the element 85 are selected to provide a narrow beamwidth (less than 10°) at this frequency. By making the elements 85 large (1"×1"), the energy is directed through the scanned article 95 to the corresponding element 85 on the opposite roller transducer assembly 97, and not to adjacent elements 85 in such opposite roller transducer assembly 97.

Referring again to FIG. 1 and FIG. 2, the immediate areas 34a, 34b, 34c around each one of the rod holes 20a, 20b, 20c in each cores section 12a, 12b, 12c are counter sunk for inserting mini-rollers or bearings 36 through which the rods 18a, 18b, 18c are inserted. The bearings 36 receive loads from a urethane tire 38 to protect the transducers 26. Without these bearings 36 the inner diameter of the tire rim might impact and damage the transducers 26. With the bearings 36 in place, an impact load is transferred via rolling contact points into the tension rods 18a, 18b, 18c and the transducer of each core section is fully protected. The fill end 14 comprises a nylon roller tube 40 comprising a plurality of holes 42 for inserting bolts for securing the end cap. Encircling the nylon roller tube 40 of the ultrasonic roller transducer assembly 10 is the urethane tire 38 which makes the contact with an object which is sensed by the transducer 26.

The urethane tire 38 is very soft (Shore A 40 durometer) to conform to the surface geometry of the article or board 96 being scanned. This minimizes reflections off of surface irregularities, and allows the energy to penetrate into the article or board 96. The tire 38 comprises isotropic materials such as polymers (for example urethane) or steel, etc., that have properties that are the same in all directions. Anisotropic materials may be employed such as composites having properties that vary in different directions to enhance signal transmission and reception. The tire profile may be varied to preferentially contact the scanned object in specific areas or from different angles. The tire 38 may be shaped to direct transmission or reception from a specific direction.

Figure 3:
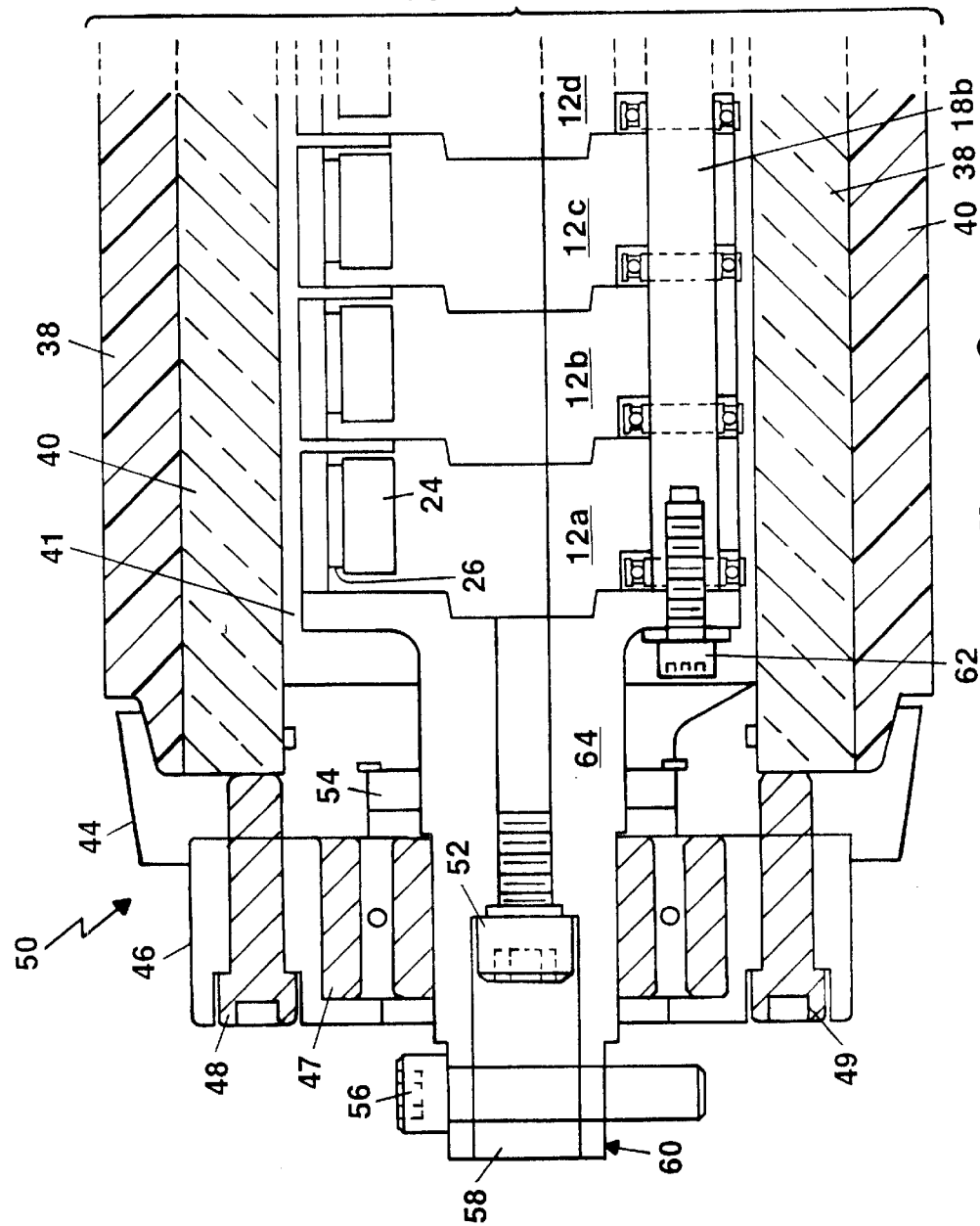
FIG. 3 is a cross-sectional view of a fill end of the ultrasonic roller transducer assembly.
Figure 4:
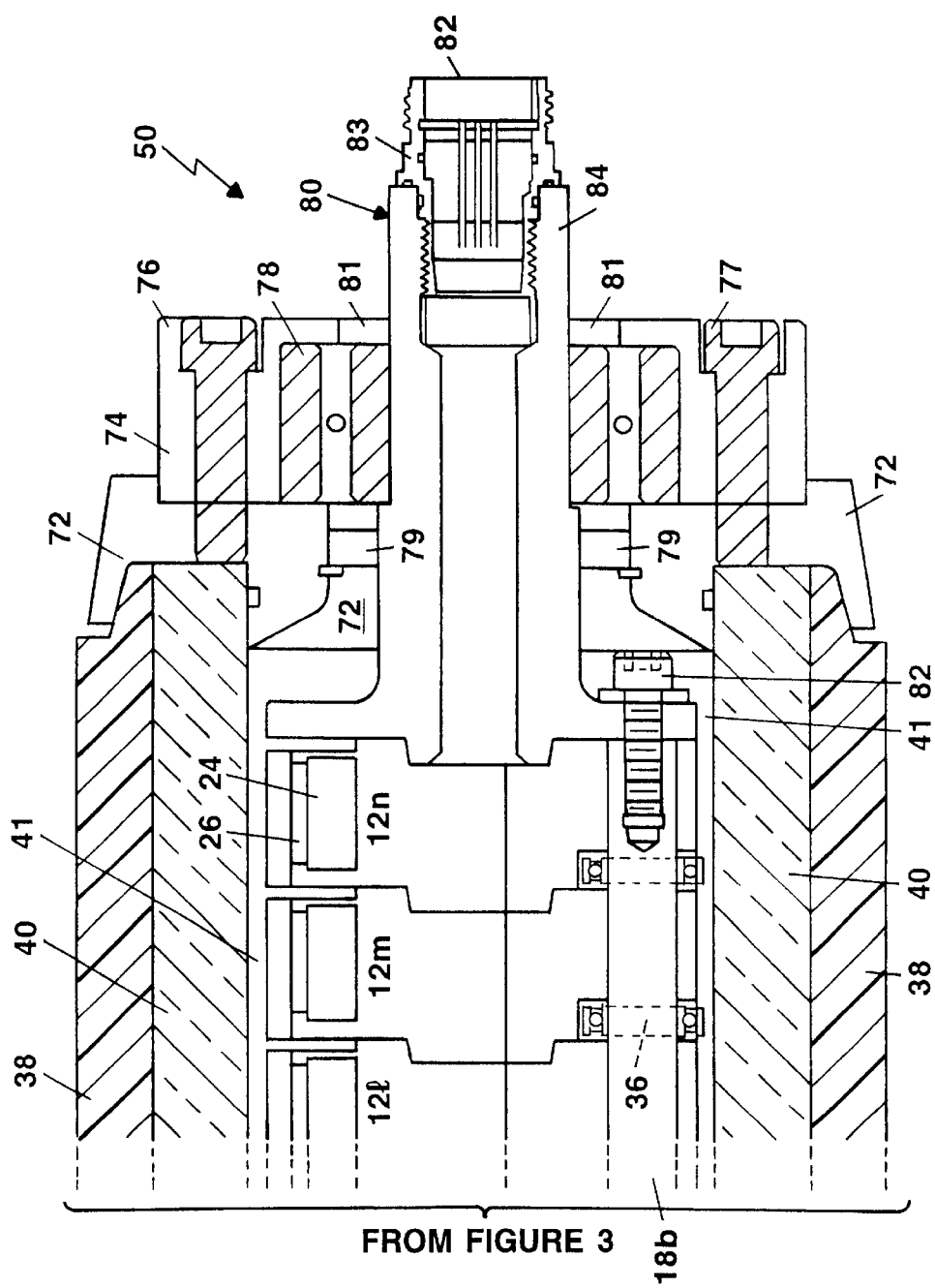
FIG. 4 is a cross-sectional view of a connector end of the ultrasonic roller transducer assembly.

Referring now to FIG. 3 and FIG. 4, FIG. 3 shows a cross-sectional view of a fill end 60 of the ultrasonic roller transducer assembly 50, and FIG. 4 shows a cross-sectional view of a connector end 80 of the ultrasonic roller transducer assembly 50. FIGS. 3 and 4 together show an ultrasonic roller transducer assembly 50 having a plurality of core sections 12a–12n. A fluid, such as silicone oil 41, is poured into the ultrasonic roller transducer assembly 50 when the seal plug 52 is removed and the transducer assembly 50 is resting on the connector end 60. The oil 41 is de-gassed to eliminate any trapped air. The oil 41 within the ultrasonic roller transducer assembly 50 provides a continuous path for the ultrasonic energy to be transmitted out of the roller transducer assembly 50 and into the scanned article or board 96.

When the seal plug 52 is screwed back in, the oil is secured within the ultrasonic roller transducer assembly 50. A hub 64 is positioned against the first core section 12a. A dynamic seal 54 is positioned around the neck of the hub 64.

An end fitting 44 is positioned over the end of the rim to protect the tire 38 from side impact loads. End rod bolts 62 are used to secure the ends of the rods 18a, 18b and 18c to the hub 64 at each end.

A main bearing 47 is a standard thrust bearing, and it is positioned around the neck of the hub 64. The main bearing 47 allows the outer portion of the assembly 50 to rotate about the core sections 12a–12n having the transducers 26.

A cap 46 is placed over the end of the hub 64 and secured by four bolts including bolts 48, 49. A bolt 56 is inserted through the end of the hub 64 to mount the roller transducer assembly 50 into position so that it can scan articles or materials such as lumber 95 as it passes by the transducer assembly 50.

Still referring to FIGS. 3 and 4, the mechanical structure of the ultrasonic roller assembly 50 includes materials in the signal transmission path that are selected to minimize attenuation and impedance mismatch. For example, when the piezoelectric elements are used for acoustic scanning, all components in the acoustic path such as core sections 12a, 12b, 12c, oil 41, rim 40, and tire 38 are acoustically transparent, i.e. they have an acoustic impedance that is similar to each other and to the material being scanned, so that there are minimal reflections at each material surface. When other measuring techniques are used, such as in optical techniques, the materials of the interfacing elements can be optically transparent because the tension rods 18a, 18b, 18c and other structural members are outside of the optical transmission path.

Referring now to FIG. 4, the connector end 80 of the ultrasonic roller transducer assembly 50 is shown. The wiring from the transducer 26 in each of the core sections 12a to 12n is fed through the wiring chase in the center of the core sections to the connector 82. Otherwise, the connector end 80 is similar to the fill end 60. An end fitting 72 is positioned adjacent to the end of the urethane tire 38 and nylon roller tube 40. The connector 82 is attached to the end of a hub 84 and the opposite end of the hub 84 is disposed adjacent to core section 12n. A dynamic seal 79 fits around the hub. The dynamic seal 79 prevents the oil fluid 41 from escaping from the assembly 50 as the end fittings 44, 72 rotate relative to the hubs 64, 84.

A main bearing 78 fits around the hub 84 which allows the outer portion of the roller transducer assembly 50 to rotate about the core sections 12a–12n comprising the transducers 26. A cap 74 is fitted against the end fitting 72, and bolts 76, 77 secure the cap 74 to the end fitting 72. End bolt 82 secures the hub 84 and the rod 18b along with two other end bolts (not shown) which secure the ends of rods 18a and 18c.

The preferred embodiment of the ultrasonic roller transducer assembly 50 for a particular sawmill application comprises the following dimensions: overall length 30 inches; outer diameter 8 inches; aperture 19.5 inches. This assembly 50 includes fourteen (14) core sections each 1.5 inches long on 2.0 inch centers. The compliant specification is 40 durometer Shore A. There is 20 db isolation between adjacent core sections, and the operating frequency is a single frequency between 10 Khz–10 Mhz, preferably at 200 Khz.

Figure 5:
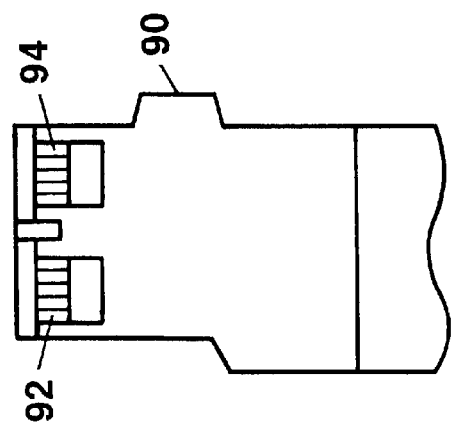
FIG. 5 is a partial side view of an alternate embodiment of a core section having two transducers.

Referring to FIG. 5, an alternate embodiment of a core section 90 of the ultrasonic roller transducer assembly 50 is shown comprising two transducers 92, 94. Multiple transducers 92, 94 within a core section 90 increase the sensitivity of the assembly 50.

Figure 8:
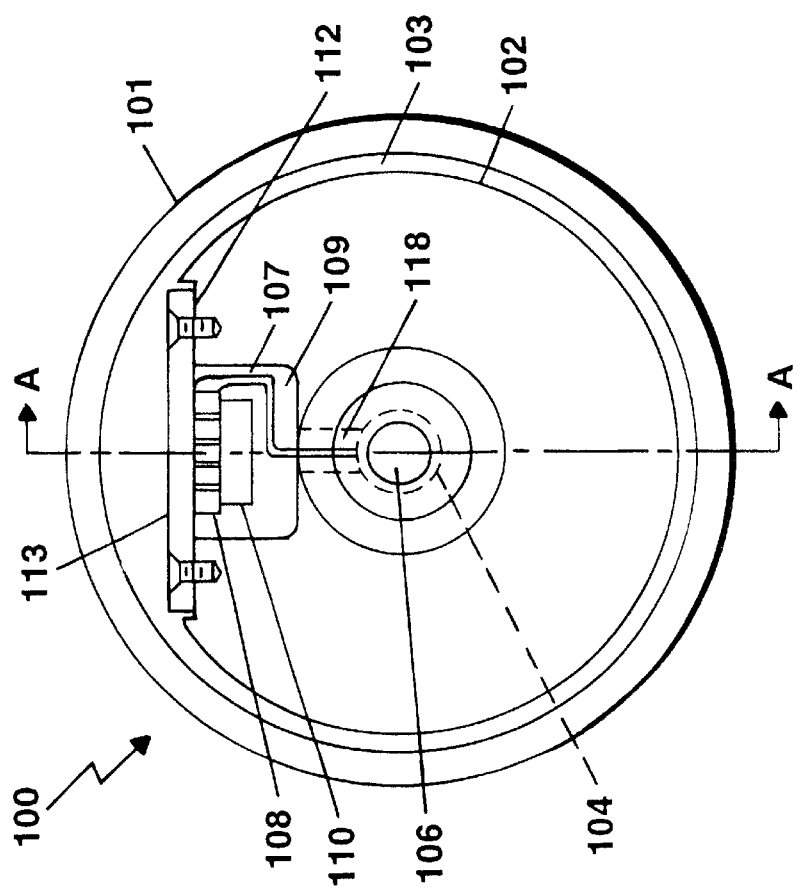
FIG. 8 is an elevational end view of a single element roller transducer having a combined core/hub assembly.

Referring now to FIG. 8, an elevational end view of a single element roller transducer 100 is shown. A roller tube 101 provides the outer portion of the roller transducer 100 and is spaced apart from a combined core/hub assembly 102 which comprises metal material such as steel. Of course a compliant tire may be attached to the roller tube 101 to conform to rough surfaces. One portion of the combined core/hub assembly 102 has a recessed flat surface 112 with a stiff polymer insert 113, such as Delrin®. A transducer assembly 110 is attached under the stiff polymer insert 113 with epoxy and electrical leads 107 from a transducer 108 are fed to the center of the roller transducer 100. A rod 106 is positioned through the hollow center 104 of the roller transducer 100. A cavity 109, which receives the transducer assembly 110, does not require a gasket or walls on sides because of the free-flooded design. A fluid 103 such as silicone oil occupies the space between the roller tube 101 and the combined core/hub assembly 102 such as immediately above the stiff polymer insert 113.

Figure 9:
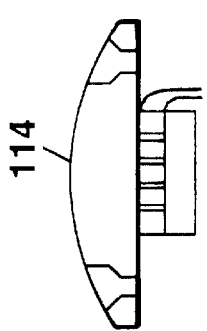
FIG. 9 is an alternate embodiment of the single element roller transducer of FIG. 8.
Figure 10:
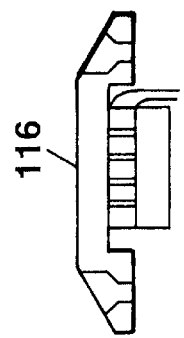
FIG. 10 is an alternate embodiment of the single element roller transducer of FIG. 8.

Referring now to FIG. 9 and FIG. 10, alternate embodiments of the stiff polymer insert 113 of FIG. 8 are shown. FIG. 9 shows a stiff polymer insert 114 that is arcuate in shape and has a transducer assembly 110 disposed under the stiff polymer insert 114, and FIG. 10 shows a stiff polymer insert 116 that is trapezoidal in shape and has a transducer assembly 110 disposed under the stiff polymer insert 116. The different insert shapes are used to minimize laminar flow of the oil within the roller transducer 100 in order to minimize pressure disturbances and resulting electrical noise.

Figure 11:
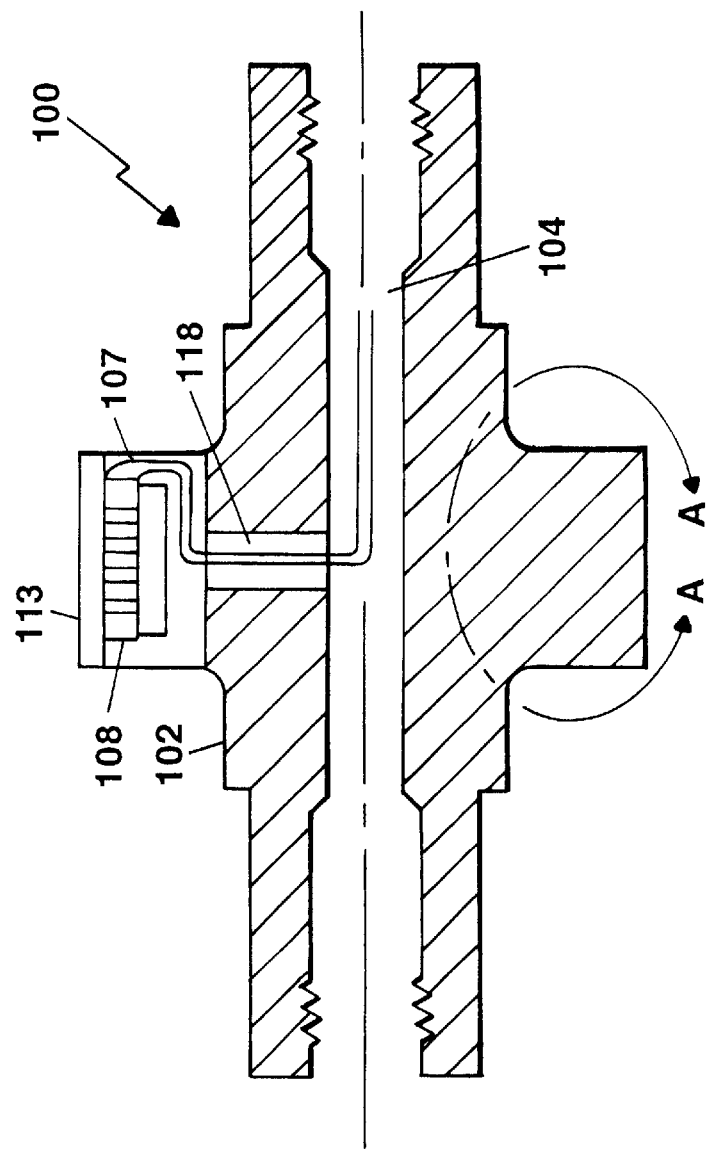
FIG. 11 is a cross-sectional view of the stationary portion of the single element roller transducer of FIG. 8.

Referring now to FIG. 11, a cross-sectional view of the stationary portion of the single element roller transducer 100 of FIG. 8 is shown without the roller tube 101 and fluid 103 elements. The piezoelectric transducer 108 is shown disposed under the stiff polymer insert 113 and the electrical leads 107 are fed through a hollow shaft 118 down to the hollow center 104 of the roller transducer 100. This single element roller transducer 100 is constructed from a single piece of material so it does not require stiffening means such as rods 18a, 18b, 18c in FIG. 1.

Figure 12:
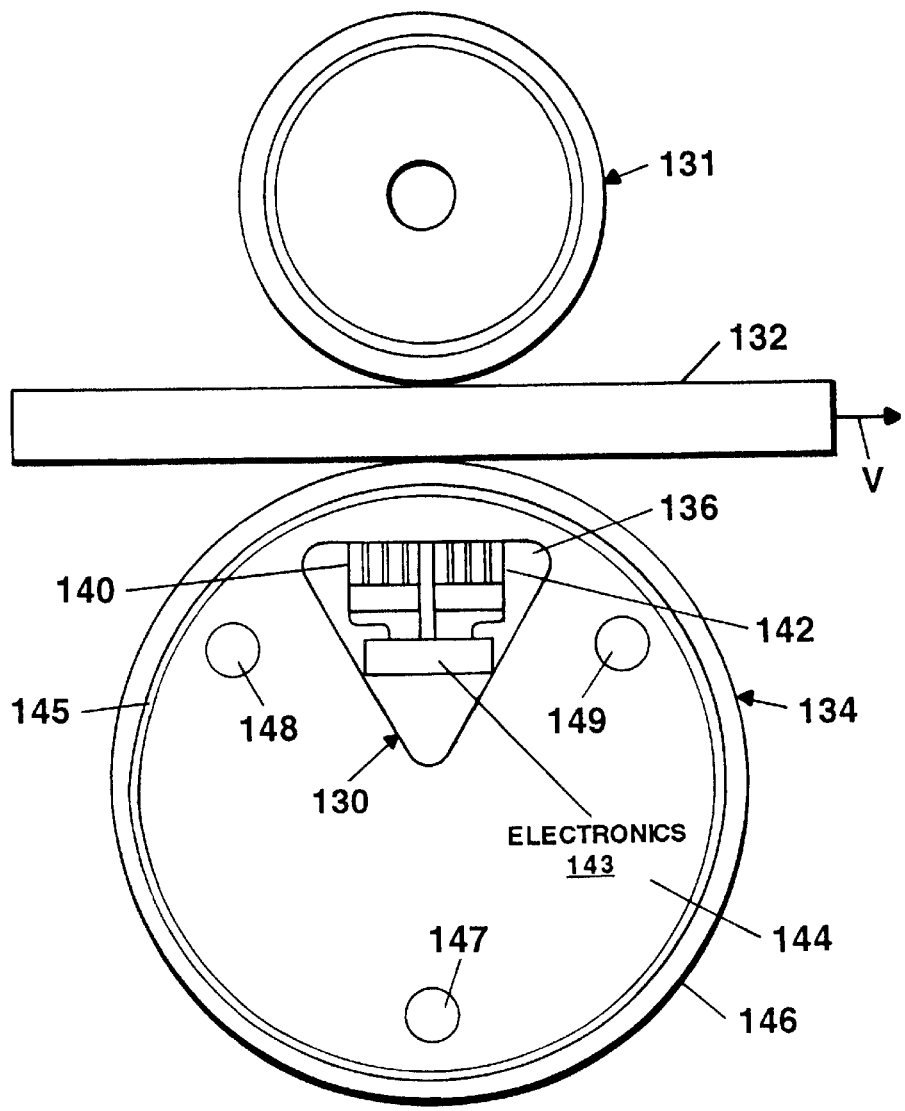
FIG. 12 is an elevational view of an acoustic velocity sensor.

Referring to FIG. 12, an acoustic velocity sensor 130 is shown located within a cavity 136 of an ultrasonic roller transducer assembly 134. An object 132 such as a wooden rectangular board travels adjacent to and in contact with the ultrasonic roller transducer 134. A roller 131 positioned opposite the ultrasonic roller transducer provides pressure against the object 132 as it travels by the roller 131. The acoustic velocity sensor 130 includes transducers 140, 142 and associated electronics 143. The transducers 140, 142 may be embodied by 1–3 piezocomposite elements, and the associated electronics 143 includes transmit electronics for sending or transmitting signals to transducer 140, and receiver electronics for receiving a return signal from transducer 142 and calculating the velocity of an object 132 passing.

The sequence of operation is as follows: first, transducer 140 transmits a signal to the object 132 and the signal is reflected from the object 132 and received by transducer 136 where it is processed by receiver electronics 143 which records the propagation time. Second, transducer 142 transmits a signal to the object 132 and the signal is reflected from the object 132 and received by transducer 140 and then processed by the electronics 143, which records the propagation time.

If the object being scanned is moving to the right as indicated by the arrow (V) in FIG. 12, then the signal propagation time from transducer 140 to transducer 142 will be less than the signal propagation time from transducer 142 to transducer 140 because the propagation medium (the core 144, oil 145 and roller tube 146) is moving away from transducer 140 and toward transducer 142. The velocity of the object 132 may be calculated because it is proportional to the difference between the two signal propagation time measurements.

This invention has been disclosed in terms of certain embodiments. It will be apparent that many modifications can be made to the disclosed apparatus without departing from the invention. Therefore, it is the intent of the appended claims to cover all such variations and modifications as come within the true spirit and scope of this invention.

What is claimed as new and desired to be secured by Letters Patent of the United States is:

1. A roller transducer assembly comprising:
   at least one core section having at least one transducer positioned in said core section to transmit or receive signals;
   means for stiffening said core section and securing said core section to a hub of said assembly;
   a roller tube surrounding and spaced apart from said core section, said roller tube being secured to each end of said assembly;
   means, sealed between said roller tube and an outer portion of each core section, for providing a continuous path for energy transfer to and from said transducer; and
   means for constraining radial and axial movement of said roller tube at least at one end while permitting rotation of said roller tube about said hub.

2. The roller transducer assembly as recited in claim 1 wherein said core section comprises means for constraining radial movement between said core section and said hub.

3. The roller transducer assembly as recited in claim 1 wherein said roller tube comprises a material for enhancing energy transfer.

4. The roller transducer assembly as recited in claim 1 wherein said roller tube comprises an outer portion of a soft material for enhancing said continuous path for energy transfer to and from said roller transducer assembly.

5. The roller transducer assembly as recited in claim 1 wherein said energy transfer means comprises a medium for efficient signal transmission.

6. The roller transducer assembly as recited in claim 1 wherein said energy transfer means comprises a fluid.

7. The roller transducer assembly as recited in claim 1 wherein each core section comprises a cavity for receiving said transducer.

8. The roller transducer assembly as recited in claim 1 wherein each core section comprises a cavity for receiving said transducer and associated electronics.

9. The roller transducer assembly as recited in claim 1 wherein each core section comprises a hollow center portion for channeling electrical leads to a connector at an end of said assembly.

10. The roller transducer assembly as recited in claim 1 wherein each core section comprises means for transferring impact loads from said roller tube to said stiffening and said securing means.

11. The roller transducer assembly as recited in claim 1 wherein said core section, said roller tube, and said energy transfer means comprise materials to minimize energy reflections at each interface of said materials.

12. The roller transducer assembly as recited in claim 1 wherein said assembly comprises a noncontinuous contact surface above said transducer to improve inter-element separation.

13. The roller transducer assembly as recited in claim 1 further comprises means for generating and processing signals to and from said transducer.

14. The roller transducer assembly as recited in claim 1 further comprises:
   a second transducer positioned adjacent to said first transducer in each core section;
   means for generating a first signal coupled to said first transducer for transmission to said object moving in a predetermined direction adjacent to said transducer assembly;
   means for detecting said first signal reflected from said moving object;
   means for generating a second signal coupled to said second transducer for transmission to said object;
   means for detecting said second signal reflected from said moving object; and
   means for calculating the velocity of said moving object from the propagation time of said detected first signal and said detected second signal sent to and reflected from said moving object.

15. An ultrasonic roller transducer assembly comprising:
   a plurality of core sections, each of said core sections comprises a transducer positioned in each of said core sections to transmit or receive signals;
   a plurality of rods, each of said rods passes through one of a plurality of rod holes on said core sections, each of said plurality of rods being secured to said assembly at each end of said rods;
   a roller tube surrounding and spaced apart from said plurality of core sections, said roller tube being secured to an end cap of said assembly;
   a tire encircling said roller tube for contacting an object;
   a fluid, sealed between said roller tube and said outer portions of said plurality of core sections, for providing a continuous path for energy transfer to and from said transducer of said core sections; and
   a bearing positioned around a neck of a hub attached to each end of said assembly enabling said tire and said roller tube to rotate about said plurality of core sections.

16. The ultrasonic roller transducer assembly as recited in claim 15 wherein each of said plurality of core sections comprises means for interlocking adjacent core sections.

17. The ultrasonic roller transducer assembly as recited in claim 15 wherein said transducer comprises an acoustic transducer made from piezoelectric material.

18. The ultrasonic roller transducer assembly as recited in claim 15 wherein said transducer comprises an acoustic transducer made from electrostrictive material.

19. The electrosonic roller transducer assembly as recited in claim 15 wherein said transducer comprises an acoustic transducer made from 1–3 electrocomposite material.

20. The ultrasonic roller transducer assembly as recited in claim 15 wherein said roller tube comprises a nylon material.

21. The ultrasonic roller transducer assembly as recited in claim 15 wherein said tire comprises a soft urethane material.

22. The ultrasonic roller transducer assembly as recited in claim 15 wherein said fluid comprises a silicone oil.

23. The ultrasonic roller transducer assembly as recited in claim 15 wherein each of said plurality of core sections comprises a cavity for receiving said transducer and a foam section disposed adjacent to said transducer for providing a low impedance backing to reflect energy out of said core sections.

24. The ultrasonic roller transducer assembly as recited in claim 15 wherein each of said plurality of core sections comprises a hollow center portion for channeling electrical leads to a connector at an end of said assembly.

25. The ultrasonic roller transducer assembly as recited in claim 15 wherein each of said plurality of core sections comprises a roller bearing positioned around each of said rods passing through said core sections for absorbing impact loads from said object.

26. The ultrasonic roller transducer assembly as recited in claim 15 wherein said plurality of core sections, said roller tube, said tire, and said fluid comprises approximately the same acoustic impedance for minimal reflections at each material interface.

27. The ultrasonic roller transducer assembly as recited in claim 15 wherein said tire comprises a plurality of notches above said transducers to improve inter-element separation.

28. The ultrasonic roller transducer assembly as recited in claim 15 further comprises means for generating and processing signals to and from said transducer.

29. The ultrasonic roller transducer assembly as recited in claim 15 further comprises:
   a second transducer positioned adjacent to said first transducer in each of said core sections;
   means for generating a first signal coupled to said first transducer for transmission to said object moving in a predetermined direction adjacent to said transducer assembly;
   means for detecting said first signal reflected from said moving object;
   means for generating a second signal coupled to said second transducer for transmission to said object;
   means for detecting said second signal reflected from said moving object; and
   means for calculating the velocity of said moving object from the propagation time of said detected first signal and said detected second signal sent to and reflected from said moving object.

30. A roller transducer comprising:
   a combined core/hub assembly having a flat surface on a portion of the circumference of said roller transducer, a hollow cylindrical center portion, and an insert secured to said flat surface;
   a cavity disposed in said roller transducer under said inset;
   a transducer assembly positioned in said cavity under said insert having electrical leads which are fed to said hollow cylindrical center portion of said roller;
   a roller tube surrounding and spaced apart from said combined core/hub assembly, said roller tube being secured at each end of said roller transducer; and
   a fluid, sealed between such combined core/hub assembly and said roller tube, for providing a continuous path for energy transfer to and from said transducer assembly.

31. The roller transducer as recited in claim 30 wherein said insert comprises a flat inner surface and a flat outer surface.

32. The roller transducer as recited in claim 30 wherein said insert comprises an outer spherical surface and an inner flat surface.

33. The roller transducer as recited in claim 30 wherein said insert comprises an outer trapezoidal surface and an inner surface having a cavity for receiving a portion of said transducer assembly.

34. The roller transducer as recited in claim 30 wherein said transducer assembly comprises a piezoelectric transducer.

35. The roller transducer as recited in claim 30 wherein said transducer assembly comprises an electrostrictive transducer.

36. The roller transducer as recited in claim 30 wherein said transducer assembly comprises a 1–3 piezocomposite transducer.

37. The method of providing a roller transducer assembly comprising the steps of:

provide at least one core section having at least one transducer positioned in each core section to transmit and to receive signals;

stiffening said core section with means extending through each core section and securing said extending means and said core section to a hub of said assembly;

positioning a roller tube around and spaced apart from each core section, said roller tube being secured to each end of said assembly;

providing a fluid between said roller tube and an outer portion of each core section to have a continuous path for energy transfer to and from said transducer; and constraining radial and axial movement of said roller tube at least at one end which permits rotation of said roller tube about said hub.

38. The method as recited in claim 37 wherein said step of providing at least one core section having at least one transducer positioned in each core section comprises the step of providing a 1–3 piezocomposite transducer for said transducer.

* * * * *